US010591472B2

(12) United States Patent
De Theije et al.

(10) Patent No.: US 10,591,472 B2
(45) Date of Patent: Mar. 17, 2020

(54) USE OF ANTIOXIDANTS IN METHODS AND MEANS FOR DETECTION OF TARGET MOLECULES IN A BLOOD SAMPLE

(71) Applicant: Minicare B.V., Eindhoven (NL)

(72) Inventors: Femke Karina De Theije, Berghem (NL); Joost Lambert Max Vissers, Nijmegen (NL)

(73) Assignee: Minicare B.V., Eindhoven (NL)

( * ) Notice: Subject to any disclaimer, the term of this patent is extended or adjusted under 35 U.S.C. 154(b) by 560 days.

(21) Appl. No.: 14/419,953

(22) PCT Filed: Aug. 8, 2013

(86) PCT No.: PCT/IB2013/056484
§ 371 (c)(1),
(2) Date: Feb. 6, 2015

(87) PCT Pub. No.: WO2014/027281
PCT Pub. Date: Feb. 20, 2014

(65) Prior Publication Data
US 2015/0226732 A1 Aug. 13, 2015

Related U.S. Application Data

(60) Provisional application No. 61/682,395, filed on Aug. 13, 2012.

(51) Int. Cl.
| G01N 33/543 | (2006.01) |
| G01N 33/78 | (2006.01) |
| G01N 33/74 | (2006.01) |
| G01R 33/12 | (2006.01) |
| G01N 33/53 | (2006.01) |

(52) U.S. Cl.
CPC ..... *G01N 33/5434* (2013.01); *G01N 33/5302* (2013.01); *G01N 33/54326* (2013.01); *G01N 33/74* (2013.01); *G01N 33/78* (2013.01); *G01R 33/1269* (2013.01)

(58) Field of Classification Search
CPC ......... G01N 33/5302; G01N 33/54326; G01N 33/5434; G01N 33/74; G01N 33/78; G01R 33/1269
See application file for complete search history.

(56) References Cited

U.S. PATENT DOCUMENTS

| 5,395,755 A | 3/1995 | Thorpe et al. |
| 2007/0077548 A1 | 4/2007 | Boger |
| 2011/0212931 A1 | 9/2011 | Tanaka et al. |

FOREIGN PATENT DOCUMENTS

| CN | 101000349 A | 7/2007 |
| CN | 101324579 A | 12/2008 |
| EP | 2052736 A1 | 4/2009 |
| EP | 2361644 B1 | 4/2014 |
| JP | 1992293506 A | 10/1992 |
| JP | 31777658 B2 | 6/2001 |
| WO | 9716967 A1 | 5/1997 |
| WO | WO 2010/061580 | * 6/2010 |
| WO | 2011077333 A1 | 6/2011 |
| WO | WO 2011/073867 A1 * | 6/2011 |

OTHER PUBLICATIONS

The International Preliminary Report on Patentability issued for the International Patent Application No. PCT/IB2013/056484, dated Feb. 17, 2015.*
Machine translation of Kashio et al., WO 2010/061580, published Jun. 3, 2010.*
Machine translation of JP 3177658 B2, published Jun. 18, 2001 (IDS submitted Feb. 6, 2015).*
Miller et al., "The relative contributions of ascorbic acid and phenolic antioxidants to the total antioxidant activity of orange and apple fruit juices and blackcurrant drink," Food Chem., 1997, vol. 60, issue 3, pp. 331-337.*
The printouts Trolox®, Aspirin®, Topanol® OC, Irganox® 1076, Ionox® 220, Ethanox® 330, Cyanox®, and Irganox® 1010 retrieved from Internet on Apr. 9, 2018.*
Bauernfeind, "Ascorbic Acid Technology in Agricultural, Pharmaceutical, Food, and Industrial Applications," in Ascorbic Acid: Chemistry, Metabolism, and Uses, 1982, Chapter 20, pp. 395-497.*
Veronique, Jarrige et al, "A fast intraoperative PTH point-of-care assay on the Philips handheld magnotech system", Langenbeck's Archives of Surgery, Springer, Berlin, DE, vol. 396, No. 3, Dec. 21, 2010, pp. 337-343, XP019885531, ISSN: 1435-2451, DOI: 10.1007/S00423-010-0733-Z.
Jimenez-Alvarez D. et al: "Antioxidant activity of oregano, parsley, and olive mill wastewaters in bulk oils and oil-in-water emulsions enriched in fish oil", Journal of Agriculural and Food Chemistry, vol. 56, No. 16, Aug. 2008, pp. 7151-7159, XP002718019, ISSN: 0021-8561.

(Continued)

Primary Examiner — Galina M. Yakovleva
(74) Attorney, Agent, or Firm — McCoy Russell LLP (57) ABSTRACT

The present invention relates to a method for detection of at least one target molecule in a blood sample comprising at least the following steps: (a) providing a blood sample; (b1) contacting said sample with an antioxidant and applying said sample to a filter to separate the blood cells from said sample; and/or (b2) applying said sample to a filter to separate the blood cells from said sample, wherein said filter comprises an antioxidant; (c) contacting said sample with a first binding molecule in the cartridge, wherein said first binding molecule is attached to a magnetic particle, and wherein said first binding molecule is capable of specifically binding to said at least one target molecule; (d) contacting said sample with a second binding molecule, wherein said second binding molecule is attached to a sensor surface, and wherein said second binding molecule is capable of specifically binding to said at least one target molecule; and (e) detecting the magnetic particles on the sensor surface. The present invention also relates to the use of an antioxidant in the process of detection of at least one target molecule in a blood sample as well as to cartridges for insertion into an assay device for detection of at least one target molecule in a blood sample.

11 Claims, 3 Drawing Sheets

(56) References Cited

OTHER PUBLICATIONS

Thorslund, Sara et al "A hybrid poly(dimethylsiloxane) microsystem for on-chip whole blood filtration optimized for steroid screening", Biomedical Microdevices, vol. 8, No. 1, pp. 73-79, 2006.
Bao Ande et al "Clinical Application of Serum PTH M Determination in Diagnosis of Secondary Hyperparathyroidism Induced by Chronic Renal Failure" Journal of China-Japan Friendship Hospital, vol. 11, No. 3, Aug. 1997—Abstract Only.

\* cited by examiner

USE OF ANTIOXIDANTS IN METHODS AND MEANS FOR DETECTION OF TARGET MOLECULES IN A BLOOD SAMPLE

CROSS-REFERENCE TO PRIOR APPLICATIONS

This application is the U.S. National Phase application under 35 U.S.C. § 371 of International Application No. PCT/IB2013/056484, filed on Aug. 8, 2013, which claims the benefit of U.S. Provisional Patent Application No. 61/682,395, filed on Aug. 13, 2012. These applications are hereby incorporated by reference herein.

FIELD OF THE INVENTION

The present invention relates to a method for detection of at least one target molecule in a blood sample. The present invention also relates to the use of an antioxidant in the process of detection of at least one target molecule in a blood sample as well as to cartridges for insertion into an assay device for detection of at least one target molecule in a blood sample.

BACKGROUND OF THE INVENTION

In vitro diagnostics is of growing importance due to the increasing demand for more effective and efficient healthcare. On the one hand, such diagnostic tests are performed in centralized laboratories, hosting a large variety of instruments which are operated by professional technicians and on the other hand, such diagnostic tests are performed in point-of-care settings outside of laboratory environments e.g. in an operation theatre, at the physician's office, at the hospital bedside, in the ambulance or at the patient's home. Point-of-care tests, in addition of being rapid, are required to be sensitive as the testing for certain disease biomarkers require detection to be completed in the range of picomolar concentrations. Using magnetic particles as labels in sandwich immunoassays has been proven to be suitable for this purpose.

For testing outside laboratory environments, it is further essential that the test be compact and robust paired with a high ease of use. Thus, there is a strong need to provide a point-of-care setting that has as few user-aided steps as possible.

OBJECTS AND SUMMARY OF THE INVENTION

The present invention addresses these needs and provides means and methods for a rapid and easy-to-use detection of at least one target molecule in a blood sample.

The above objective is in particular accomplished by a method for detection of at least one target molecule in a blood sample comprising at least the following steps: (a) providing a blood sample; (b1) contacting said sample with an antioxidant and applying said sample to a filter to separate the blood cells from said sample; and/or (b2) applying said sample to a filter to separate the blood cells from said sample, wherein said filter comprises an antioxidant; (c) detecting the target molecule. In one embodiment, detection of the target molecule comprises the steps of (c1) contacting said sample with a first binding molecule in the chamber of the cartridge, wherein said first binding molecule is attached to a magnetic particle, and wherein said first binding molecule is capable of specifically binding to said at least one target molecule; (c2) contacting said sample with a second binding molecule, wherein said second binding molecule is attached to a sensor surface, and wherein said second binding molecule is capable of specifically binding to said at least one target molecule; and (c3) detecting the magnetic particles on the sensor surface.

One advantage is that the detection of a target molecule in a blood sample can be performed without a centrifugation step. The blood cells are removed from the blood sample by means of filtration. A disposable cartridge, which can be inserted in a handheld assay device, may thus be equipped with a dedicated filter such that the user only needs to add the blood sample to the cartridge in which all pre-treatment and reagents necessary for the test are already presented.

However, it has been observed that for target molecules such as parathyroid hormone (PTH), filtration of the blood sample may result in a decreased assay response compared to plasma obtained by centrifugation. It has been found that addition of an antioxidant to the sample increases assay response for a filtrated blood sample. In particular, the examples of the present application demonstrate that addition of an antioxidant leads to a correlation of about 1 for test results obtained from blood and plasma. That means the assay response is the same for blood obtained by removing the blood cells by filtration and plasma obtained by centrifugation.

Without wishing to be bound to a theory one possible explanation for the observed decrease in assay performance of a filtered blood sample is that upon contact of the target molecule with the filter and/or blood cells that are concentrated during filtration, the target molecule becomes oxidized and as a result is more difficult to detect, e.g. is not anymore recognized by the binding molecule. In that way, the target molecule is not recognized in the assay occurring in the sample container. The antioxidant added to the blood sample protects the target molecule against oxidation.

In a preferred embodiment of the present invention the steps (c1) and (c2) of the method as described above are performed at the same time.

In a further aspect the present invention relates to the use of an antioxidant in the process of detection of at least one target molecule in a blood sample involving a first binding molecule attached to a magnetic particle and a second binding molecule attached to a sensor surface, wherein said first binding molecule and said second binding molecule are capable of specifically binding to said at least one target molecule.

In yet another aspect the present invention relates to a cartridge for insertion into an assay device for detection of at least one target molecule in a blood sample, comprising: (i) an antioxidant and (ii) a filter to remove blood cells. In one embodiment, the cartridge may further comprise (iii) a first binding molecule attached to a magnetic particle; and (iv) a second binding molecule attached to a sensor surface, wherein said first binding molecule and said second binding molecule are capable of specifically binding to said at least one target molecule.

In another preferred embodiment of the present invention the antioxidant is incorporated into the filter of the cartridge as described above.

In a further preferred embodiment of the present invention the cartridge as described above further comprises a reductant.

In yet another preferred embodiment of the present invention the cartridge as described above is for use in a handheld assay device.

In a preferred embodiment of the herein above mentioned method, use or cartridge of the present invention, said one target molecule is parathyroid hormone.

In another preferred embodiment of the herein above mentioned method, use or cartridge of the present invention, said antioxidant is a phenolic antioxidant.

In yet another preferred embodiment of the herein above mentioned method, use or cartridge of the present invention, said antioxidant is selected from the group comprising ascorbic acid, sodium metabisulfite, sodium citrate, Trolox®, 5-bromo-5-nitro-1,3-dioxane, ethoxyphenol, phenyl salicylat, vitamin A, vitamin E, BSA, melatonin, alpha-carotene, beta-carotene, Aspirin®, Topanol® OC, Irganox® 1076, Ionox® 220, Ethanox® 330, Cyanox® 2246 and Irganox® 1010.

In a further preferred embodiment of the herein above mentioned method, use or cartridge of the present invention, said first binding molecule is an antibody or a fragment thereof.

In yet another preferred embodiment of the herein above mentioned method, use or cartridge of the present invention, said second binding molecule is an antibody or a fragment thereof.

In a further preferred embodiment of of the herein above mentioned method, use or cartridge of the present invention, said magnetic particle has a size of 10 to 1000 nm.

In another preferred embodiment of the herein above mentioned method, use or cartridge of the present invention, said magnetic particles are superparamagnetic particles.

In yet another preferred embodiment of the herein above mentioned method, use or cartridge of the present invention, said detection is carried out using frustrated total internal reflection.

BRIEF DESCRIPTION OF THE DRAWINGS

FIG. 1 shows as schematic representation (side view) of an exemplary optomagnetic device suitable for detection of at least one target molecule within a blood sample. Such a device typically comprises a light source (LED) emitting an input light beam, a light detector (photodetector) for detecting and measuring an output light beam, and connected thereto an evaluation unit. The input light beam is emitted into the sample container (which typically is located in a cartridge) comprising a sensor surface made from glass or a transparent plastic. Further, the sample container comprises the fluid sample to be tested and magnetic particles, for instance, superparamagnetic beads, which are functionalized with a binding molecule for detection of a target molecule and which can be magnetically actuated by an upper (washing magnet) and a lower magnet (binding magnet). The presence of magnetic beads at a sensor surface "frustrates" the total internal reflection of a light beam, resulting in a reduction of the reflected light proportional to the number of magnetic particles located near or on the sensor surface of the sample container.

FIG. 2 shows the signal change (%) resulting from the experiments as described in Example 1. Addition of the antioxidant sodium metabisulfite causes a significant increase of the assay response for filtered blood samples, resulting in a blood-plasma correlation of about 1. The reference samples show that in the absence of antioxidant the blood-plasma correlation is only about 0.5.

FIG. 3 shows the signal change (%) resulting from the experiments as described in Example 2. Addition of the antioxidant ascorbic acid causes a significant increase of the assay response for filtered blood samples, resulting in a blood-plasma correlation of about 1. The reference samples show that in the absence of antioxidant the blood-plasma correlation is only about 0.5.

DETAILED DESCRIPTION OF THE EMBODIMENTS

The present invention relates to methods and means for direct use of a blood sample for detection of at least one target molecule.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein, as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

For testing outside laboratory environments, ideally, the user only needs to add the sample to a disposable cartridge and all pre-treatment and reagents necessary for the test are already present in the cartridge. Therefore, to be able to perform a simple, reliable, blood-based point-of-care test, the blood cells need to be separated without a centrifugation step. For this aim, the cartridge is equipped with a dedicated filter. The requirement for such a point-of-care setting is a blood-plasma correlation of about 1. This means the assay response is the same for blood obtained by removing the blood cells by means of filtration and plasma obtained by centrifugation.

However, the inventors found that for detection of parathyroid hormone the correlation between blood and plasma is about 0.5 which is insufficient for a quantitative, blood based application. The inventors found that adding antioxidants resulted in a large boost in the assay signal for blood, resulting in similar assay performance for blood and plasma and thereby resulting in a blood-plasma correlation of about 1.

As has been set out above, the present invention concerns in one aspect a method for detection of at least one target molecule in a blood sample comprising at least the following steps: (a) providing a blood sample; (b1) contacting said sample with an antioxidant and applying said sample to a filter to separate the blood cells from said sample; and/or (b2) applying said sample to a filter to separate the blood cells from said sample, wherein said filter comprises an antioxidant; (c) detecting the target molecule. Detection may take place by different approaches. For example, detection may be achieved by a direct assay, a competitive assay, a sandwich assay etc. all of which may use different binding moleculy. For example, a binding molecules such as a labeled antibody or a labeled ligand, which is specific for the target molecule, may be used to directly detect the target molecule. The label may e.g. be a fluorescent label, radioactive label, a chemical label for luminescent detection, an affinity tag label etc. In another approach, the target molecule may be contacted with an unlabeled binding molecule such as an antibody or ligand. The established interaction between the target molecule and the unlabeled binding molecule may then detected by competition with a e.g. labeled compound which is known to compete with the interaction of the target molecule and the unlabeled binding molecule. Such a labeled compound may be a labeled antibody, ligand, small molecule etc. all of which bind to the target molecule with a higher affinity than the unlabeled binding molecule. The labels may be same as described above. In a further embodiment, a sandwich assay using two binding molecules which recognize different sites of the target molecule can be used to detect the target molecule. Such sandwich assay which make use of e.g. two different antibodies can be employed to facilitated detection by e.g. magnetic beads. In one embodiment, detection of the target molecule thus comprises at least the steps of (c1) contacting said sample with a first binding molecule, wherein said first binding molecule is attached to a magnetic particle, and wherein said first binding molecule is capable of specifically binding to said at least one target molecule; (c2) contacting said sample with a second binding molecule, wherein said second binding molecule is attached to a detection surface, and wherein said second binding molecule is capable of specifically binding to said at least one target molecule; and (c3) detecting the magnetic particles on the sensor surface.

A "target molecule" as used herein may be any molecule which can be bound by a binding molecule and may for example be a biological substance such as a biomolecule, complexes, cell fractions or cells. Preferably, a target molecule within the context of the present invention is a nucleic acid, e.g. DNA, or RNA molecule or an oligonucleotide such as a DNA or RNA oligonucleotide. Even more preferred are target molecules such as a peptide, a protein, a drug molecule, a small molecule, or a vitamin. In particular preferred embodiments of the present invention a "target molecule" may be a biomarker.

The term "biomarker" as used herein can be defined as a characteristic that is objectively measured and evaluated as an indicator of normal biological processes, pathogenic processes or pharmacologic responds to a therapeutic intervention. The biomarker molecules envisaged by the present invention can be any biomarker known in the art such as disease-related biomarker or drug-related biomarker. Disease-related biomarkers provide an indication of the probable effect of treatment on patient (risk indicator or predictive biomarkers), if a disease already exists (diagnostic biomarker), or how such a disease may develop in an individual case regardless of the type of treatment (prognostic biomarker). A predictive biomarker generally helps to assess the most likely response to a particular treatment, whereas prognostic markers are used to monitor the progression of a disease with or without treatment. In contrast, drug-related biomarkers indicate whether a drug will be effective in a specific patient and how the patient's body will process it. The skilled person is aware of numerous novel biomarkers used in the various and highly specified medical fields.

In another preferred embodiment of the present invention the biomarker is selected from the group selected from nucleic acids, proteins and metabolites. A biomarker may thus refer to a molecule, preferably a protein, measured in a blood sample whose concentration reflects the severity or presence of some disease state. Thus, a biomarker can be used as an indicator of a particular disease state or also a physiological state of an organism.

In a further preferred embodiment of the present invention the target molecule is a hormone. Preferred examples of hormones are melatonin, serotonin, thyroxine, triiodothyronine, epinephrine, norepinephrine, dopamine, antimullerian hormone, adrenocorticotropic hormone, adiponectin, angiotensin, angiotensinogen, antidiuretic hormone, atrial-natriuretic peptide, calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, growth hormone, human placental lactogen, inhibin, insulin, insulin-like growth factor, leptin, luteinizing hormone, melanocyte stimulating hormone, orexin, oxytocin, parathyroid hormone, prolactin, relaxin, secretin, somatostatin, thyroid-stimulating hormone, thyrotropin-releasing hormone, cortisol, aldosterone, testosterone, dehydroepiandrosterone, androstenedione, dihydrotestosterone, estradiol, estrone, estriol, progesterone, calcitriol, calcidiol, prostaglandins, leukotrienes, prostacyclin, thromboxane, prolactin releasing hormone, lipotropin, brain natriuretic peptide, neuropeptide y, histamine, endothelin, pancreatic polypeptide, rennin and enkephalin. In principle, the methods, uses and cartridges as described herein are suitable to detect target molecules which are susceptible to oxidation. Parathyroid hormone may be preferred as a target molecule.

In a particularly preferred embodiment of the present invention the target molecule which is subjected to a detection method or use of the present invention or which is to be detected with the help of a cartridge as described herein is parathyroid hormone.

A "blood sample" as used herein refers to a blood sample which includes target molecules as defined herein. Such samples may, for example, include samples taken from an individual or a patient. The blood sample may be whole blood, the whole blood sample can be untreated or treated, e.g. may contain anticoagulants. Plasma obtained by centrifugation of a blood sample is not to be understood as a blood sample.

In a further preferred embodiment of the present invention the blood sample is taken from an individual, wherein the blood sample is an untreated whole blood sample.

In some embodiments, target molecules such as biomarker are directly obtained from blood samples. In other situations samples may be first subjected to sample preparation techniques, e.g. based on standard protocols, including, for example, partial purification, which renders the target molecules more accessible to binding partners, i.e. a first and second binding molecule as defined herein. In other preferred embodiments additives are added to the blood sample which render the target molecules more accessible to binding partners or which are needed for quantification of an assay response.

The term "providing a blood sample" as used herein means that the blood sample is provided outside the human or animal body.

An "antioxidant" as used herein refers to a molecule capable of slowing or preventing the oxidation of other molecules. In a preferred embodiment of the invention the antioxidant is a phenolic antioxidant. Examples for phenolic antioxidants are Topanol® OC, Irganox® 1076, Ionox® 220, Ethanox® 330, Cyanox® 2246, Irganox® 1010. In another preferred embodiment of the invention the antioxidant is ascorbic acid, sodium metabisulfite, Trolox®, 5-bromo-5-nitro-1,3-dioxane, ethoxyphenol, phenyl salicylat, vitamin A, vitamin E, BSA, melatonin, alpha-carotene, beta-carotene, Aspirin®, Topanol® OC, Irganox® 1076, Ionox® 220, Ethanox® 330, Cyanox® 2246 or Irganox® 1010. The present invention also envisages further antioxidants which would be known to the person skilled in the art or can be derived from suitable literature sources. The present invention also envisages antioxidants which are not yet know or may be known to the skilled person in the future.

A "filter" as used herein refers to filter capable of separating blood cells from the blood sample. Typically such a filter shows good separation of blood cells, low hemolysis, no retention of the target molecule and no modification of the target molecule in the filter. In a preferred embodiment the filter is a Vivid® Plasma Separation GF Membrane from PALL. The filter may be treated or untreated. In a preferred embodiment the filter is treated with a filter treatment buffer. Suitable buffers for the treatment are known to the skilled person and include sugar, salt, a buffering agent, proteins and a surfactant. In a particularly preferred embodiment the treatment buffer in another preferred embodiment the filter may further comprise reagents to improve assay performance.

In a preferred embodiment of the invention the antioxidant is contacted with the blood sample before applying the blood sample to the filter. In an alternative embodiment the filter may already comprise the antioxidant. The final concentration of the antioxidant in the sample may be in a range which results in a blood-plasma recovery for the target molecule of interest of 1±20%, preferably ±15%, more preferably ±10%, and even more preferably ±5%.

The term "blood-plasma recovery" as used herein refers to a single number that describes the degree of relationship between two assay responses resulting from blood on the one hand and plasma on the other hand. The term "plasma" as used herein refers to a plasma sample obtained by centrifugation of a blood sample. The term "blood" as used herein refers to the liquid part of a blood sample that is obtained after the blood sample has been applied to a filter to separate the blood cells. The blood-plasma recovery is determined by dividing the quantitative assay response resulting from blood by the quantitative assay response resulting from plasma. Exemplarily, a quantitative assay response may be a change in light signal resulting from the location of magnetic particles near or on a sensor surface or may be the calculated concentration of the target molecule. The blood-plasma recovery is about 1, if the two assay responses are in the same range. The blood-plasma recovery is about 0.5 if the assay response resulting from plasma is about twice as high as the assay response resulting from blood. The target molecule may preferably be a hormone such as parathyroid hormone.

In a preferred embodiment the final concentration of the antioxidant in the sample is of about 0.01 M to about 5 M, preferably in a range of about 0.05 M to about 2 M, e.g. at a concentration of about 0.05 M, about 0.1 M, about 0.2 M, about 0.3 M, about 0.4 M, about 0.5 M, about 0.7 M, about 1.0 M, about 1.2 M, about 1.5 M, about 1.7 M, or about 2.0 M. In a particular preferred embodiment the concentration of the antioxidant in the sample is 0.12 M.

In a preferred embodiment the antioxidant is contacted with the blood sample before applying the sample to the cartridge, exemplarily in a dedicated blood tube or pipette.

In another preferred embodiment the antioxidant is integrated in the cartridge.

In a specific embodiment of the present invention the antioxidant may be incorporated into the filter by adding the antioxidant to the filter treatment buffer.

In a further preferred embodiment, the antioxidant may be incorporated into the filter by treatment of the filter in a non-oxidizing environment (e.g. under $N_2$ flow).

In another preferred embodiment the antioxidant is added in a dry form to the filter.

In yet another embodiment of the invention the antioxidant is added to another position in the cartridge. Exemplarily, the antioxidant may be added to the bead drying buffer.

In a specific embodiment of the invention the contacting of the antioxidant with the blood sample results in blood-plasma recovery of 1±20%, preferably ±15%, more preferably ±10%, and even more preferably ±5%.

In another specific embodiment of the invention the antioxidant is sodium metabisulfite or ascorbic acid.

In another preferred embodiment of the invention sodium metabisulfite is added to the blood sample in a final concentration of 0.12 M.

In yet another embodiment of the invention ascorbic acid is added to the blood sample in a final concentration of 0.12 M.

A "reductant" as used herein refers to a molecule capable of reducing other molecules. For instance, target molecules which were oxidized can be reduced by a reductant. In a preferred embodiment of the invention the reductant is sodium metabisulfite, ascorbic acid and L-cysteine. The present invention also envisages further reductants which would be known to the person skilled in the art or can be derived from suitable literature sources. The present invention also envisages reductants which are not yet know or may be known to the skilled person in the future.

In another preferred embodiment, the cartridge according to the invention further comprises a reductant.

In a preferred embodiment of the invention, the reductant is incorporated in any part of the cartridge, e.g. the reductant is incorporated in the filter.

A "magnetic particle" as used herein means a small, localized object to which can be ascribed a physical property such as volume or mass. The term "magnetic particles" shall comprise both permanently magnetic particles as well as magnetisable particles. Furthermore, a particle essentially behaves as a whole unit in terms of its transport and properties. Magnetic particles may accordingly be of a symmetrical, globular, essentially globular or spherical shape, or be of an irregular, asymmetric shape or form.

The size of a magnetic particle envisaged by the present invention typically ranges between 3 nm and 50 µm. Preferred are magnetic particles in the nanometer and micrometer range up to several micrometers. Even more preferred are particles in the size of 10 to 1000 nm. Particularly preferred are magnetic nanoparticles, e.g. particles with a diameter of about 10 to 700 nanometers. Particularly preferred are nanoparticles which may have a diameter of about 10 to 600 nm, e.g. 10 nm, 15 nm, 20 nm, 25 nm, 30 nm, 35 nm, 40 nm, 45 nm, 50 nm, 60 nm, 70 nm, 80 nm, 90 nm, 100 nm, 120 nm, 150 nm, 170 nm, 200 nm, 220 nm, 250 nm, 270 nm, 300 nm, 320 nm, 350 nm, 370 nm, 400 nm, 420 nm, 450 nm, 470 nm, 500 nm, 520 nm, 550 nm, 570 nm, 600 nm, 620 nm or any value in between. Even more preferred are nanoparticles having a diameter of about 500 nm.

In a preferred embodiment, the magnetic particles are superparamagnetic particles. In a particular preferred embodiment, the magnetic particles are superparamagnetic beads.

The term "superparamagnetic" as used herein describes a form of magnetism which appears in small ferromagnetic or ferrimagnetic nanoparticles. It is known in the art that in sufficiently small nanoparticles, magnetization can randomly flip direction under the influence of temperature. The time between two flips is referred to as the Neel relaxation time. In the absence of an external magnetic field, when the time used to measure the magnetization of the nanoparticles is much longer than the Neel relaxation time, the magnetization appears to be in average zero, i.e. in the paramagnetic state. In such a state an external magnetic field is able to magnetize the nanoparticles similarly to a paramagnet. However, the magnetic susceptibility is much larger than those of paramagnets.

The magnetic particle according to the present invention is functionalized with a first binding molecule, which can be attached to the magnetic particle directly or indirectly, i.e. via a spacer or linker.

A "sensor surface" as used herein, defines an area for detection and may be typically located within a sample container. The sample container may be located in a cartridge. The sensor surface may serve for the detection of at least one target molecule within a blood sample and is typically made of glass or transparent plastics. For such a detection of at least one target molecule, the sensor surface is functionalized with a second binding molecule, which can be attached to the sensor surface directly or indirectly, i.e. via a spacer or linker. Location of the magnetic particles near or on the sensor surface causes a change in light signal.

As used herein, the term "change in light signal" means a difference in light reflected from the magnetic particles which is detected by optical means. For instance, such methods may include methods such as the detection of scattered light or detection based on total internal reflection (TIR) or frustrated total internal reflection (FTIR). Preferably, the change in light signal refers to only those magnetic particles being close or at the sensor surface. Such a measurement typically requires that the magnetic particles within the area of detection are hampered in their movement, i.e. have become substantially immobilized or have entirely lost mobility. In absence of magnetic particles no refraction occurs and the light beam from the light source is totally reflected. If a magnetic particle is close to the sensor surface or is in contact with the sensor surface the light rays are said to be frustrated by the particle and reflection at that point is no longer total.

The signal, which may be defined as the decrease of the totally internal reflected signal, can be calculated. The signal is more or less linearly dependent on the concentration of particles on the sensor surface (surface density n). The signal can be expressed as:

$$S=\beta \bar{n},$$

wherein S is the measured signal change in % and $\beta$ is a conversion factor from surface density to signal change.

It is envisaged by the present invention that a single sample be subjected to different simultaneous or timely separated detection assays. For this purpose, the sample container may comprise magnetic particles which are uniformly functionalized, i.e. all magnetic particles are coated with the same first binding molecule for capturing the target. Alternatively, also the sample container may comprise at least two, at least three or several differentially functionalized particles. Accordingly, the sensor surface has to be adapted to carry out such a multiple detection platform.

The term "binding molecule" as used herein refers to any molecule having a high binding affinity for a second molecule, i.e. an interaction partner. A binding molecule in the sense of the present invention typically comprises binding or capture moieties capable of binding a specific target molecule, preferably a biomarker, or capable of binding a molecule-containing target entity, such as for example a virus, or a cell or a cell fragment, or material derived from tissue.

In a particularly preferred embodiment, the binding molecule is selected from the group consisting of aptamers, peptides, proteins, oligonucleotides, and molecular imprinted polymers, wherein said binding molecule preferably is an antibody or a fragment thereof.

An "aptamer" as used within the context of a binding molecule may be a short nucleic acid molecule, e.g. an RNA, DNA, PNA, CNA, HNA, LNA or ANA molecule or any other suitable nucleic acid format known to the person skilled in the art, being capable of binding to a target molecule as defined herein. Furthermore, the present invention envisages peptide aptamers, i.e. aptamers which are able to specifically bind to (a) protein(s), polypeptide(s) or peptide(s) comprising a specific amino acid sequence(s). Typically, (a) peptide aptamer(s) is/are a variable peptide loop(s), comprising for example 10 to 20 amino acids. In the context of the present invention the peptide aptamer(s) may in specific embodiments be attached at one or both ends to a scaffold structure. The scaffold structure may be any molecule, preferably a protein, e.g. a protein, which has good solubility properties. Suitable scaffold molecules would be known to the person skilled in the art. An example of suitable scaffold molecule to be used in the context of the present invention is the bacterial protein thioredoxin-A. The aptamer peptide loop may preferably be inserted within a reducing active site of the scaffold molecule. Alternatively, staphylococcal protein A and domains thereof and derivatives of these domains, such as protein Z or lipocalins may be used as scaffold structures in the context of the present invention. Nucleic acid or peptide aptamers may be generated according to any suitable method known to the person skilled in the art, e.g. via PCR or molecular synthesis approaches or yeast two-hybrid approaches.

A "peptide" as used within the context of a binding molecule may comprise a stretch of 2 to 35 amino acids, amino acid derivatives or a mixture thereof. The peptide may be linear, branched, circular or mixture thereof. A peptide binding may also be attached to a scaffold structure as defined herein above.

A "protein" as used within the context of a binding molecule may comprise a stretch of more than about 35 amino acids, amino acid derivatives or a mixture thereof. The protein may have a linear, branched, circular form or be comprised of a mixture of these forms. A protein binding molecule may also be attached to a scaffold structure as defined herein above.

An "oligonucleotide" as used within the context of a binding molecule may comprise a stretch of about 5 to 120 nucleotides, e.g. a stretch of 10, 20, 30, 40, 50, 60, 70, 80, 90 or 100 nucleotides, preferably of about 15 to 60 nucleotides. An oligonucleotide affinity molecule may preferably be an RNA molecule or a DNA molecule, or a mixture of both.

The term "molecular imprinted polymer" as used herein refers to a polymer which was formed in the presence of a molecule that is extracted afterwards, leaving complementary cavities behind. Typically, a molecular imprinted polymer shows a certain chemical affinity for the original molecule. A molecular imprinted polymer may be composed of any suitable polymeric unit known to the person skilled in the art. Techniques for their production include polymerization techniques such as bulk, precipitation, emulsion, suspension, dispersion, gelation, and multi-step swelling polymerization. Particularly preferred are hierarchical imprinting methods.

An "antibody" as used within the context of a binding molecule refers to an immunoglobulin molecules and immunologically active portions of immunoglobulin molecules, i.e. molecules that contain an antigen binding site that immunospecifically binds an antigen. The immunoglobulin molecules of the invention can be of any type (e. g., IgG, IgE, IgM, IgD, IgA and IgY), class (e. g., IgG1, IgG2, IgG3, IgG4, IgA1 and IgA2) or subclass of immunoglobulin molecules. Antibodies of the present invention may be described or specified in terms of the epitope(s) or portion(s) of a polypeptide of the present invention which they recognize or specifically bind. Specific epitopes and their interaction with antibodies would be known to the person skilled in the art. The term "specifically binding" as used herein refers to the immunospecific detection and binding of an antibody to an antigenic epitope. The term "specifically binding" excludes non-specific binding but does not necessarily exclude cross-reactivity with other antigens, in particular with antigens comprising the same antigenic epitope detected by the present antibody.

The antibody may be a polyclonal, monoclonal, multispecific, human, humanized or chimeric antibody, single chain antibody, or constitute a Fab fragment, Fab' fragment, a fragment produced by a Fab expression library, F(ab')2, Fv, disulfide linked Fv, minibody, diabody, scFv, sc(Fv)2, whole immunoglobulin molecule, small modular immunopharmaceutical (SMIP), binding-domain immunoglobulin fusion protein, camelized antibody, $V_{HH}$ containing antibody, an anti-idiotypic (anti-Id) antibody an any epitope-binding fragment(s) of any of the above. Most preferably, the antibodies are human antigen-binding antibody fragments of the present invention and include Fab, Fab' and F(ab')2, Fv, single-chain Fvs (scFv), sc(Fv)2, single-chain antibodies, disulfide-linked Fvs (sdFv) and fragments comprising either a VL or VH domain.

The antibodies according to the invention may be of any animal origin including birds and mammals. Preferably, the antibodies are human, murine (e. g., mouse and rat), donkey, monkey, rabbit, goat, guinea pig, camel, horse, or chicken antibodies.

The antibodies according to the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. Preferred are monospecific antibodies.

A "sample container" as used herein refers to a container in which a sample is measured. The magnetic particles as described herein may be already present in the sample container. The sample container further comprises a sensor surface which is typically made of glass or transparent plastics. The sample container may further be located in an exchangeable cartridge, i.e. in a standalone component separate from the sensor device. Due to possible contamination with a sample, such a cartridge will usually be a disposable item, made for instance from plastics by injection moulding.

A biosensor assay is used for "the detection of at least one target molecule." Such assays can be used for rapid, sensitive and easy-to-use molecular diagnostics, especially to detect biological targets. Such an assay may involve magnetic forces acting on magnetic particles functionalized with a first binding molecule capable of recognizing and binding the biological target in the sample.

In a first phase of such an assay, the magnetic particles coated with the first binding molecule move through the sample solution for effective target molecule capture. Subsequently, actuating magnets are engaged to move and transport the magnetic particles with high speed to the sensor surface for binding. Typically, attached to the sensor surface are second binding molecules also capable of binding the biological target. Thereafter, a sequence of finely tuned magnetic pulses is applied to facilitate optimal binding and mixing of the magnetic particles that have captured the target molecules. After the particles have bound to the sensor surface, free and non-specifically bound particles are rapidly removed by applying a magnetic field oriented away from the sensor surface, herein also referred to as washing magnet. The presence and/or amount of the magnetic particles bound at the sensor surface can be detected optically, wherein the number of bound magnetic particles is directly or inversely related to the amount of target molecules present in the sample, preferably the optical detection is based on frustrated total internal reflection (FTIR). Preferred detection assays envisaged by the present invention are antibody-based immunoassays such as competitive and non-competitive immunoassays.

The term "competitive immunoassay" refers to immunoassays, wherein the target molecule in the sample competes with a labeled target molecule to bind to antibodies or binding molecules. The amount of labeled target molecule bound to the antibody or binding molecule is then measured. In this method, the response will be inversely related to the concentration of target molecule in the sample. This means that the greater a response, the less target molecule in the sample was available to compete with the labeled target molecule.

The term "non-competitive immunoassay" also referred to as the "sandwich immunoassay" refers to immunoassays, wherein the target molecule in the sample to be tested is bound to a first antibody or binding molecule and further to a second antibody or binding molecule. Using the detection principle as described herein, the amount of magnetic particles bound to the second antibody or binding molecule is a suitable measure for determining the amount of target molecules. In contrast to the competitive method, the results of the non-competitive method will be directly proportional to the concentration of the target molecule.

In another preferred embodiment of the present invention the first binding molecule is an antibody or a fragment thereof as defined herein above.

In a further preferred embodiment of the present invention the second binding molecule is an antibody or a fragment thereof. Preferred examples of a second binding molecule are antibodies or antibody fragments or variants as defined herein above, which specifically bind a target molecule, preferably a biomarker molecule captured by a first binding molecule. In the case the first binding molecules are antibodies, the antibodies may bind to different epitopes of a target molecule than the first binding molecule, or may detect an epitope generated by a specific binding of the target molecule to a first binding molecule.

In another preferred embodiment of the present invention the detection of the at least one target molecule is performed using a sandwich immunoassay.

In yet a further preferred embodiment of the present invention the detection of the at least one target molecule is performed using a 1-step sandwich immunoassay.

Figure 1:
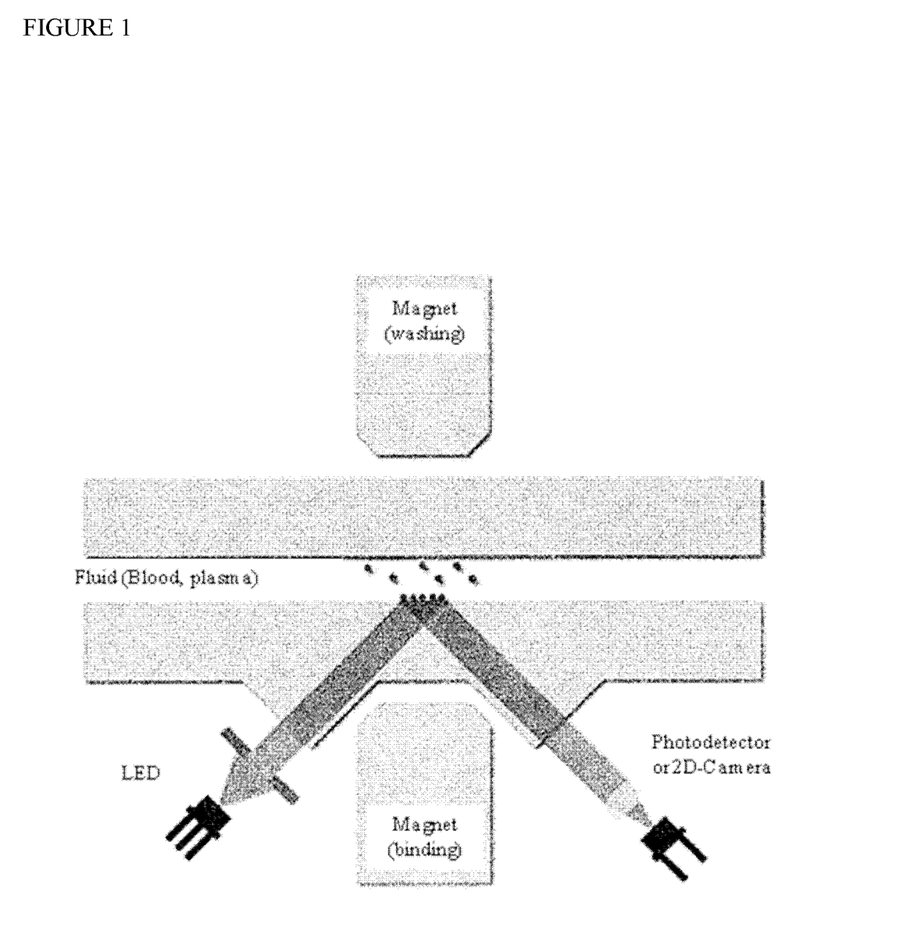

An "assay device" as used herein is typically an opto-magnetic biosensor device. Suitable devices for the detection method according to the present invention have been previously disclosed, for instance, in WO 2008/155716. In a preferred embodiment, the assay device is a handheld assay device. In particular preferred embodiments of the present invention, the Magnotech® biosensor system is used. It will be however appreciated that the detection principle underlying the present invention is not restricted to the Magnotech® system. In principle, also any other optomagnetic detection system may be used which satisfies the minimal criteria as depicted in FIG. 1. Typically, a suitable optomagnetic system may comprise a light source (LED) emitting an input light beam, a light detector (photodetector) for detecting and measuring an output light beam, and connected thereto an evaluation unit. The device further comprises a cartridge for introducing and measuring a sample. The cartridge further comprises a sample container which may further comprise magnetic particles which can be functionalized with a binding molecule such as an antibody for detection of one or more target molecules within the blood sample. Typically, the optomagnetic device comprises at least two magnets for magnetic actuation of the beads. In an exemplary arrangement, the biosensor device may comprise a magnetic field generator preferably comprising an upper (washing magnet) and a lower magnet (binding magnet). The presence of magnetic beads at a sensor surface in the sample container can be detected using such an optomagnetic sensor system.

The following examples and figures are provided for illustrative purposes. It is thus understood that the example and figures are not to be construed as limiting. The skilled person in the art will clearly be able to envisage further modifications of the principles laid out herein.

EXAMPLES

Example 1—Determination of the Influence of Sodium Metabisulfite on the Blood-Plasma Correlation An exemplary detection of a target molecule in a blood sample according to the invention is carried out on the Magnotech®-biosensor system using a detection based on frustrated total internal reflection (FTIR). The system consists of a handheld analyzer instrument and a disposable self-contained cartridge. All assay reagents necessary for the detection of a target molecule are contained in the cartridge. Once a droplet of the sample is applied, the sample is automatically drawn into the cartridge by capillary forces. There, magnetic nanoparticles functionalized with antibodies bind to the target molecule and serve as labels for the detection. Magnetic forces are used to transport the magnetic nanoparticles to the sensor surface, which is also functionalized with antibodies to which the target molecule can bind. The experimental setup is depicted in FIG. 1. Magnetic actuation of the magnetic particles occurs via the alternate action of two magnets, i.e. an upper magnet (washing magnet) and a lower magnet (binding magnet). Light is projected on the surface of the cartridge at an angle that is slightly shallower than the critical angle, causing a reflection that is imaged on a camera sensor. When nanoparticles do bind on the sensor surface, some of the light is reflected and scattered resulting in a decreased intensity compared to a measurement in the absence of magnetic particles.

The superparamagnetic beads have a diameter of 500 nm and are functionalized with anti-N-terminal PTH antibodies and the sensor surface was functionalized with anti-C-terminal PTH antibody.

A blood sample from a healthy donor was spiked with 400 pg/ml PTH and sodium metabisulfite was added in concentrations of 0.0125 M up to 0.2M (0.0125 M, 0.025 M, 0.05 M, 0.1 M and 0.2 M). These samples were added to cartridges including the blood-separating filter. A blood sample without sodium metabisulfite served as a reference. The reference was further processed in two different ways: "plasma" was generated by centrifugation of the blood samples and "blood" refers to the liquid part obtained by filtration of the blood samples. The Vivid® Plasma Separation GF Membrane from PALL was used as a filter. Before the blood sample was applied to the membrane, the membrane was pretreated with a buffer. Next, each of the samples generated either by centrifugation or filtration was applied to the above described cartridge and measured in the above described hand held analyzer. Immediately after the sample is drawn into the cartridge actuation is started and the labeled target molecule is detected on the cartridge surface after 8 minutes. Signal change resulting from the binding of the magnetic particles to the sensor surface is proportional to the amount of target molecules and is used to determine the blood-plasma recovery.

Figure 2:
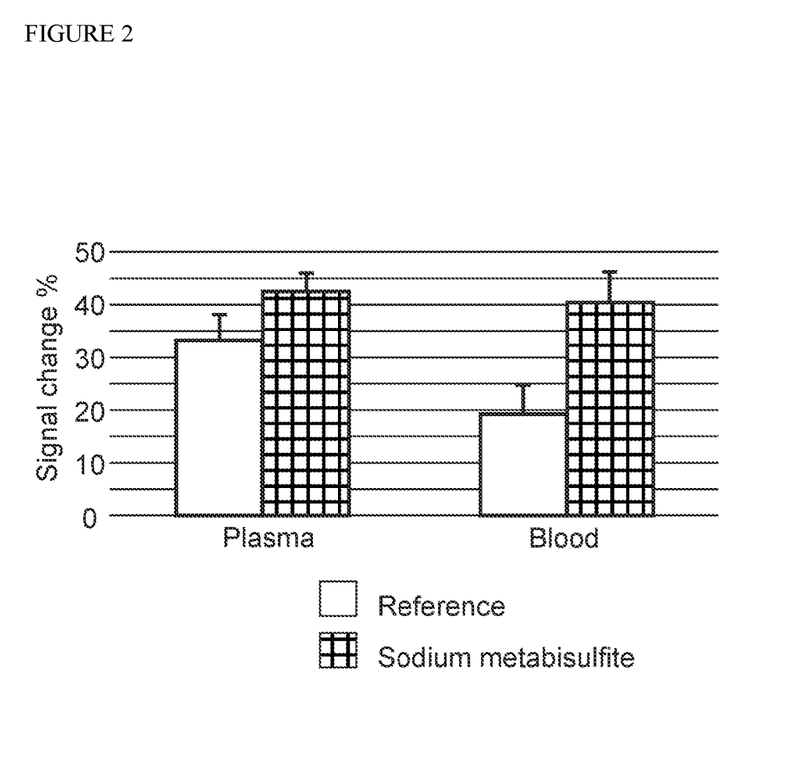

FIG. 2 shows exemplarily the measurements of a blood sample to which sodium metabisulfite was added in a concentration of 0.12 M. Additionally, references without sodium metabisulfite were measured. For each sample type (plasma with sodium metabisulfite, plasma without sodium metabisulfite, blood with sodium metabisulfite, blood without sodium metabisulfite) the measurement of the target molecule PTH was performed in triplicates. The blood-plasma correlation was determined by dividing the mean signal change resulting from blood by the mean signal change resulting from plasma. For the reference (i.e. blood and plasma without sodium metabisulfite) the correlation is about 0.5. However, when sodium metabisulfite was added to the samples, a large boost in assay signal for blood was observed. Thus, the assay performance for blood and plasma are similar and a correlation of about 1 can be achieved.

Not only the addition of sodium metabisulfite in a concentration of 0.12 M but also in concentrations of 0.05M and 0.1M resulted in a blood-plasma correlation of about 1.

Example 2—Determination of the Influence of Ascorbic Acid on the Blood-Plasma Correlation The same measurement as exemplified in Example 1 can be carried out using ascorbic acid instead of sodium metabisulfite.

Figure 3:
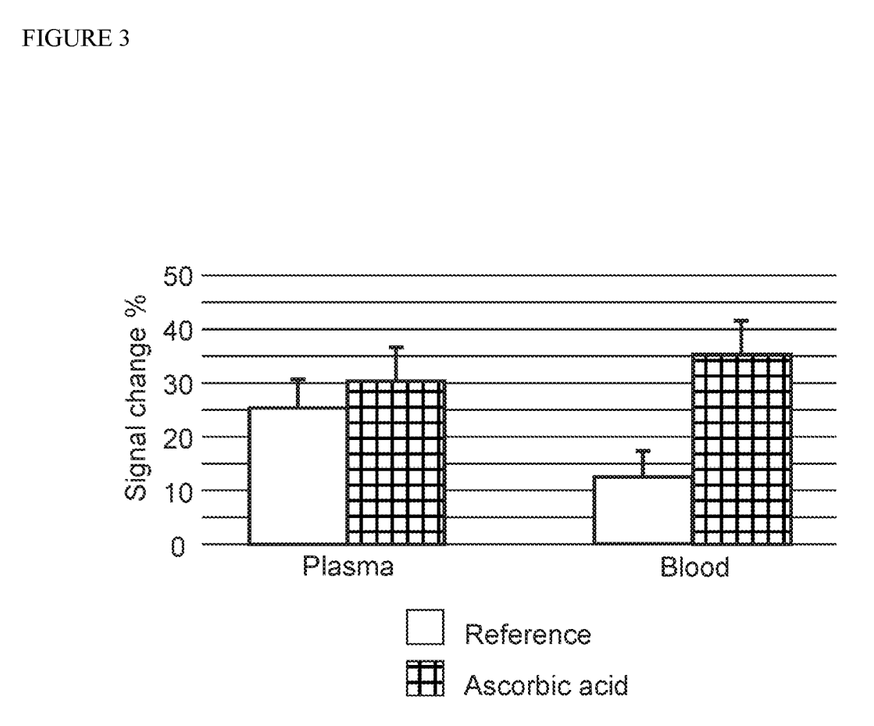

FIG. 3 shows exemplarily the measurements of a blood sample to which ascorbic acid was added in a concentration of 0.12 M. Additionally, references without ascorbic acid were measured. For each sample type (plasma with ascorbic acid, plasma without ascorbic acid, blood with ascorbic acid, and blood without ascorbic acid) the measurement of the target molecule PTH was performed in triplicates. The blood-plasma correlation was determined as described above. Again, for the reference (i.e. blood and plasma without ascorbic acid) the correlation is about 0.5. When ascorbic acid was added to the samples, a large boost in assay signal for blood was observed. Thus, the assay performance for blood and plasma are similar and a correlation of about 1 can be achieved.

Not only the addition of ascorbic acid in a concentration of 0.12 M but also in concentrations of 0.05 M and 0.1 M resulted in a blood-plasma correlation of about 1.

The invention claimed is:

1. A method for detection of at least one target molecule in a blood sample comprising at least the following steps:
   providing a blood sample;
   (b1) contacting said sample with 0.05 M to 0.12 M of an antioxidant and applying said sample to a filter to separate blood cells from said sample; and/or
   (b2) applying said sample to said filter to separate the blood cells from said sample, wherein said filter comprises said antioxidant;
   (c) detecting the target molecule, wherein detection of the target molecule comprises at least the steps of:
     (c1) contacting said sample with a first binding molecule, wherein said first binding molecule is attached to a magnetic particle, and wherein said first binding molecule is capable of specifically binding to said at least one target molecule;
     (c2) contacting said sample with a second binding molecule, wherein said second binding molecule is attached to a sensor surface, and wherein said second binding molecule is capable of specifically binding to said at least one target molecule; and
     (c3) detecting magnetic particles on the sensor surface, wherein said antioxidant is ascorbic acid or sodium metabisulfite.

2. The method according to claim 1, wherein the steps (c1) and (c2) are performed at the same time.

3. A cartridge for insertion into an assay device, comprising:
   (i) 0.05 M to 0.12 M of an antioxidant contained within the cartridge, wherein said antioxidant is ascorbic acid or sodium metabisulfite;
   (ii) a filter, wherein the filter separates blood cells from a blood sample and the blood sample is a whole blood sample;
   (iii) a sample container in which at least one target molecule in the blood sample is measured;
   (vi) a first binding molecule attached to a magnetic particle and contained within the sample container; and
   (v) a second binding molecule attached to a sensor surface within the sample container, wherein said first binding molecule and said second binding molecule are capable of specifically binding to the at least one target molecule;
   wherein the cartridge is configured in at least cartridge proportions to be inserted into the assay device and is configured to detect the at least one target molecule in the blood sample.

4. The cartridge according to claim 3, wherein the antioxidant is incorporated into the filter of the cartridge.

5. The cartridge of claim 3, wherein the cartridge is configured to be inserted into the assay device, wherein the assay device is a handheld assay device.

6. The cartridge according to claim 3, wherein said at least one target molecule is a parathyroid hormone.

7. The cartridge according to claim 3, wherein said first binding molecule is an antibody or a fragment thereof.

8. The cartridge according to claim 3, wherein said second binding molecule is an antibody or a fragment thereof.

9. The cartridge according to claim 3, wherein the cartridge contains 0.1 M of the antioxidant.

10. The cartridge of claim 9, wherein the antioxidant is sodium metabisulfite.

11. The cartridge of claim 9, wherein the antioxidant is ascorbic acid.

* * * * *